United States Patent [19]

Suido et al.

[11] Patent Number: 5,223,404

[45] Date of Patent: Jun. 29, 1993

[54] COMPOSITION FOR TESTING PERIODONTAL DISEASES

[75] Inventors: Hirohisa Suido, Osaka; Akira Miike, Shizuoka; Kenji Hasegawa, Osaka; Norihiko Kayahara, Kanagawa; Toru Eguchi, Osaka; Toshio Tatano, Shizuoka; Koichi Nakashima, Osaka, all of Japan

[73] Assignees: Sunstar Kabushiki Kaisha, Osaka; Kyowa Medex Co., Ltd., Tokyo, both of Japan

[21] Appl. No.: 639,742

[22] Filed: Jan. 11, 1991

Related U.S. Application Data

[63] Continuation of Ser. No. 298,965, Jan. 19, 1989, abandoned.

[30] Foreign Application Priority Data

Jan. 20, 1988 [JP] Japan .................................. 63-10241
Dec. 28, 1989 [JP] Japan .................................. 63-331988

[51] Int. Cl.$^5$ .............................................. C12Q 1/37
[52] U.S. Cl. ........................................ 435/24; 435/18; 435/23; 435/29; 435/34; 435/810; 530/300; 530/330; 530/331; 530/802
[58] Field of Search ............... 435/18, 23, 24, 29, 435/34, 810; 530/300, 330, 331, 802

[56] References Cited

U.S. PATENT DOCUMENTS 4,675,290 6/1987 Matsumoto et al. .................. 435/24
4,681,841 7/1987 Matsumoto et al. .................... 435/4

FOREIGN PATENT DOCUMENTS 252747 1/1988 European Pat. Off. .
255341 2/1988 European Pat. Off. .
304871 3/1989 European Pat. Off. .

OTHER PUBLICATIONS

Suido, H., et al., Journal of Periodontal Research, vol. 22, pp. 412–418 (1987).
Biological Abstracts, vol. 69, No. 3, Abstract No. 64154 (1979).

Primary Examiner—Johnnie R. Brown
Assistant Examiner—Elli Peselev
Attorney, Agent, or Firm—Wegner, Cantor, Mueller & Player

[57] ABSTRACT

A composition for testing periodontal diseases which diagnoses or prognosticates contraction or progress of the diseases or diagnoses the therapeutic value by promptly determining peptidase-like enzymatic activity in a specimen. The composition is a combination of a compound of the formula [1] or [2] or a mixture thereof, a chromogen and an oxidase:

$$X\text{-}T\text{-}Pro\text{-}Y \qquad [1]$$

or $$X'\text{-}Z'\text{-}Arg\text{-}Y' \qquad [2]$$

wherein Pro is proline residue; Arg is arginine residue; X and X' are hydrogen or an amino protecting group, respectively; Y and Y' are a residue of a compound which can increase oxidation reaction rate of a chromogen with a oxidase in the presence of oxygen and is attached to the C-terminal of Pro or Arg, respectively; and T and Z' are an amino acid or peptide residue composed of 0 to 4 amino acids or their protected derivatives the C-terminal of which is attached to the N-terminal of Pro or Arg, respectively.

3 Claims, No Drawings

COMPOSITION FOR TESTING PERIODONTAL DISEASES

This application is a continuation of U.S. application Ser. No. 07/298,965 filed Jan. 19, 1989, now abandoned.

FIELD OF THE INVENTION

The present invention relates to a composition for testing periodontal diseases. More particularly, it relates to a composition which can detect certain pathogenic oral microorganisms for periodontal diseases specifically, readily and promptly to diagnose or prognosticate contraction or progress of such diseases, or diagnose the therapeutic value.

BACKGROUND OF THE INVENTION

Recently, bacteriological researches on periodontal diseases have advanced and, as the results, it has been found that many spirochetes are detected in sites with periodontal diseases and have good correlation with various clinical indices. Further, it has been also found that anaerobic gram negative bacterial are main pathogenic oral microorganisms for periodontal diseases. Among them, Black-pigmented Bacteroides such as *Bacteroides gingivalis* are particularly noted and many reports about their pathogenicities are present.

Then, attempts are made to detect these pathogenic bacteria in the oral cavity and apply the results to clinical use so that periodontal diseases can be prevented or treated by prognosticating or diagnosing contraction or progress thereof.

However, there are some drawbacks in detection of these pathogenic oral bacteria by a bacteriological method. For example, detection requires highly skilled technique and special equipment such as use of a dark field microscope and handling of anaerobes, and involves complicated operations. Further, it takes a long time and requires skill in cultivation and for analysis of the result. Therefore, there are still difficulties in application to clinical practice.

From the immunological point of view, some attempts are made to detect the presence of the pathogenic microorganisms by determining antibody titer in blood which is humoral immunity to the pathogenic microorganisms, or determining lymphocyte blast formation which is cellular immunity. However, preparation of a specimen requires complicated operations and practical application is still difficult.

Under these circumstances, the present inventors have studied intensively to make detection of the pathogenic oral microorganisms for periodontal diseases applicable to clinical practice possible. As the result, the present inventors have found that some spirochetes in the oral cavity have very specific peptidase-like enzymatic activities and that Black-pigmented Bacteroides such as *B. gingivalis*, *B. intermedius* and the like also have similar activities. These can be detected specifically, readily and promptly by a color reaction using particular substrates with precisely reflecting periodontal disease conditions as disclosed in pending patent applications (Japanese Patent Application Nos. 61-179716, 61-233848 and 62-113122).

Separately, the present inventors have found peptidase-like enzyme can be extremely readily and promptly determined using particular compounds which can promote the color development reaction and already filed a patent application (Japanese Patent Application No. 62-286559).

OBJECTS OF THE INVENTION

The present inventors have further studied and have found that the compound which can promote such color development reaction is applicable to the detection of the above pathogenic oral microorganisms for periodontal diseases and the detection can be accomplished more readily and promptly.

The main object of the present invention is to provide an improved composition for testing periodontal diseases which diagnoses or prognosticates contraction or progress of such diseases, or diagnoses therapeutic effect by promptly determining peptidase enzymatic activity in a specimen.

This object as well as other objects and advantages of the present invention will become apparent to those skilled in the art from the following description.

SUMMARY OF THE INVENTION

According to the present invention, there is provided a composition for testing periodontal diseases which diagnoses or prognosticates contraction or progress of said diseases or diagnoses the therapeutic value by promptly determining peptidase enzymatic activity in a specimen, said composition comprises a combination of (a) a compound of the formula:

$$X\text{-}T\text{-}Pro\text{-}Y \qquad (1)$$

wherein Pro is proline residue; X is hydrogen or an amino protecting group; Y is a residue of a compound which can increase oxidation reaction rate of a chromogen with a oxidase in the presence of oxygen and is attached to the C-terminal of Pro (hereinafter referred to as an enhancer); and T is an amino acid or peptide residue compose of 0 to 4 amino acids or their protected derivatives the C-terminal of which is attached to the N-terminal of Pro, (b) a compound of the formula:

$$X'\text{-}Z'\text{-}Arg\text{-}Y' \qquad (2)$$

wherein Arg is arginine residue; X' is hydrogen or an amino protecting group; Y' is an enhancer residue which is attached to the C-terminal of Arg; and Z' is an amino acid or peptide residue composed of 0 to 4 amino acids or their protected derivatives the C-terminal of which is attached to the N-terminal of Arg, or a mixture of (a) and (b), (c) a chromogen, and (d) an oxidase.

DETAILED DESCRIPTION OF THE INVENTION

The test using the composition of the present invention includes two reaction systems. The first one is a reaction of a peptidase enzyme in a specimen with the substrates of the formulas (1) and (2) to liberate the enhancer. The second one is a reaction to oxidize the chromogen by an enzyme which can oxidize the chromogen in the presence of oxygen and in the presence of the free enhancer to generate a pigment. In the first reaction, the enhancer is generated in proportion to the peptidase enzymatic activity in the specimen. In the second reaction, the amount of the enhancer is in proportion to the generation rate of the pigment. That is, the chromogen is oxidized by the action of the oxidase and the pigment is generated with time. The generation rate of the pigment is amplified in the presence of the enhancer. The amount of the pigment generated after a certain period of time is in proportion to the amount of the enhancer.

Accordingly, by combining two reactions and determining the pigment generated, the amount of the enhancer is determined and, therefore, peptidase activity in the specimen is determined.

By using the composition of the present invention, the amount of the produced pigment can be determined by the reaction of a specimen such as saliva, dental plaque, gingival crevicular fluid or the like with the substrates of the formulas (1) and (2), preferably, under the optimal conditions (pH 5 to 9) followed by the reaction with the chromogen and oxidase, or a reaction of a specimen with the substrates of the formulas (1) and (2) in the presence of the chromogen and oxidase to readily and promptly diagnose or prognosticate contraction or progress of periodontal diseases or diagnose the therapeutic value.

The compounds of the formulas (1) and (2) used as the substrate in the present invention are known or, at least, readily prepared by known peptide synthesis. In the formulas (1) and (2), the amino protecting groups represented by X and X' may be any amino protecting group known in peptide synthesis such as formyl, acetyl, succinyl, t-butoxy-carbonyl, benzoyl, carbobenzoxy, p-toluenesulfonyl and the like.

T group may be any amino acid or peptide residue which is composed of 0 to 4 amino acids or their protected derivatives wherein C-terminal is attached to N-terminal of the proline residue. Preferably, the C-terminal amino acid in the group T is glycine, alanine, lysine, phenylalanine or their protected derivatives. The protected derivative includes OH-protected serine, SH-protected cycteine, β- or γ-COOH protected aspartic acid or glutamic acid, for example, protected with benzyl.

Z' group may be any amino acid or peptide residue which is composed of 0 to 4 amino acids or their protected derivatives wherein C-terminal is attached to N-terminal of the arginine residue. Preferably, the C-terminal amino acid in the group Z' is glycine, lysine, arginine, phenylalanine or their protected derivatives. The protected derivative includes OH-protected serine, SH-protected cycteine, β- or γ-COOH blocked aspartic acid or glutamic acid, for example, protected with benzyl.

The enhancer residues of Y and Y' may be any one which can increase oxidation reaction rate of the chromogen. The typical examples of such an enhancer include aniline derivatives of the formula:

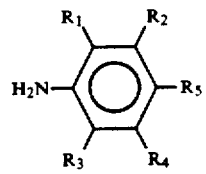

(3)

wherein $R_1$–$R_4$ are the same or different and are hydrogen, halogen, alkyl having 1 to 4 carbon atoms, sulfone or hydroxyl; and $R_5$ is hydroxyl, amino or amino substituted with alkyl having 1 to 4 carbon atoms, sulfoalkyl having 1 to 4 carbon atoms or hydroxylalkyl having 1 to 4 carbon atoms, or diaminostilbene-disulfonic acid such as 3,3'-diaminostilbene-4,4'-disulfonic acid (DSOA).

The typical examples of the compound of the formula (3) include, 3,5-dibromo-4-hydroxyaniline, (DBHA), 3,5-dichloro-4-hydroxyaniline, (DIHA), 3,5-diiodo-4-hydroxylaniline, p-p-N,N-disulfoproylaminoaniline(-SPA), phenylenediamine (PPD), 4-aminoaniline-3-sulfonic acid (DAS), 2-methyl-3,5-dibromo-4-hydroxyaniline (MDBHA), 2,6-dimethyl-3,5-dichloro-4-hydroxyaniline (DMDCHA), 4-N,N-disulfopropylamino-3,5-dibromoaniline (SDBA), 4-(N-ethyl-N-hydroxylethylamino)-3,5-dibromoaniline (EHDBA), 4-N,N-diethylamino-3,4-dihydroxyaniline (DEDHA) and the like.

The configuration of each amino acid residue in the compounds of the formulas (1) and (2) is not specifically limited so far as it can be served as the substrate or an peptidase enzyme.

As the oxidase used in the present invention, any enzyme which can oxidize the chromogen in the presence of oxygen to produce pigment may be used. For example, bilirubin oxidase (BLOD, EC1, 3, 3, 5), monophenol oxygenase (MPO, EC1, 14, 18, 1), ascorbate oxidase (AOD, EC1, 10, 3, 3), catechol oxidase (EC1, 10, 3, 1), laccase (EC1, 10, 3, 2), o-aminophenol oxidase (EC1, 10, 3, 4), 3-hydroxyanthranilate oxidase (EC1, 10, 3, 5), phenol-2-monooxygenase (EC1, 14, 13, 7) and the like.

As the chromogen, any substance which can develop color by oxidation can be used. To improve sensitivity, those with high molecular extinction coefficient are preferred. However, compounds which show less color development in the absence of the enhancer (corresponding to a blank test), but show significant color development in the presence of the enhance are preferred. Such a chromogen includes, for example, the following compounds:

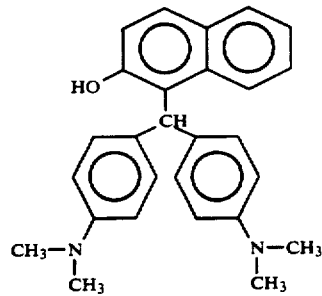

P-1

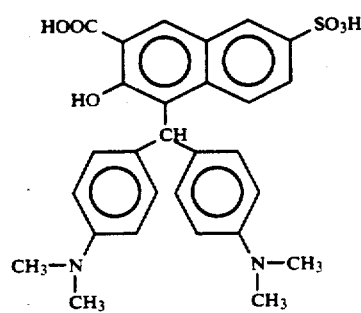

P-2

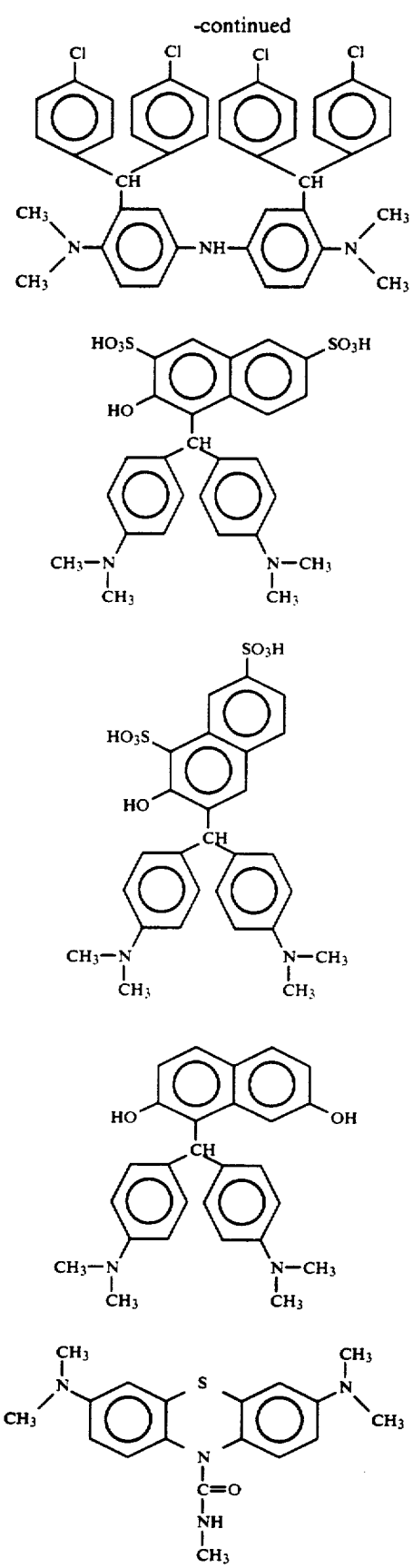
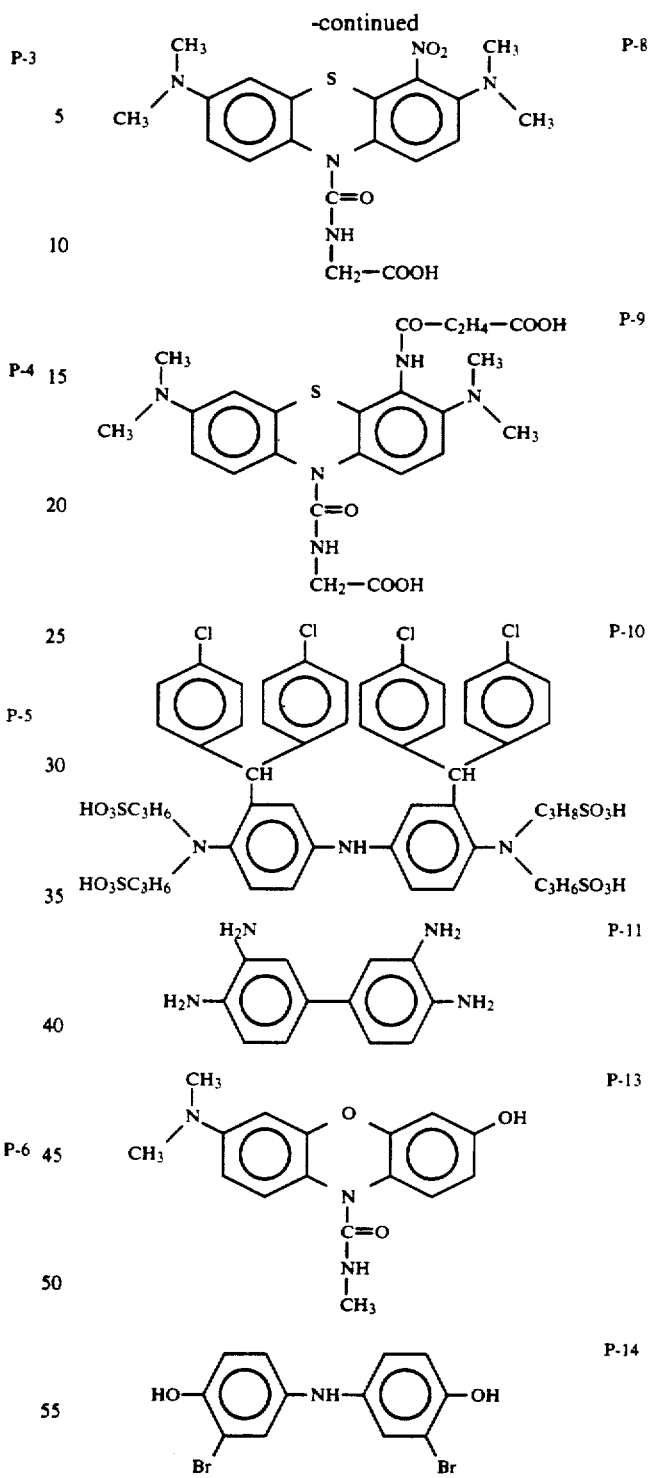
Maximum absorption of those compounds are shown in the following table.
| Pigment No. | Compound Name | Maximum Absorption (nm) |
|---|---|---|
| P-1 | 4,4'-Bis(dimethylamino)diphenyl-(2-hydroxy-1-naphthyl)methane | 630 |
| 2 | 4,4'-Bis(dimethylamino)diphenyl-(2-hydroxy-3- | 630 |

-continued

| Pigment No. | Compound Name | Maximum Absorption (nm) |
|---|---|---|
| | carboxy-6-sulfonyl-1-naphthyl)methane | |
| 3 | Bis[3-bis(4-chlorophenyl)methyl-4-dimethylaminophenyl]amine | 755 |
| 4 | 4,4'-Bis(dimethylamino)diphenyl-(2-hydroxy-3,6-disulfo-1-naphthyl)methane | 630 |
| 5 | 4,4'-Bis(dimethylamino)diphenyl-(3-hydroxy-4,6-disulfo-2-naphthyl)methane | 630 |
| 6 | 4,4'-Bis(dimethylamino)diphenyl-(2,7-dihydroxy-1-naphthyl)methane | 630 |
| 7 | 10-N-Methylcarbamoyl-3,7-dimethylamino-10H-phenothiazine | 666 |
| 8 | 10-N-Carboxymethylcarbamoyl-6-nitro-3,7-dimethylamino-10H-phenothiazine | 655 |
| 9 | 10-N-Carboxymethylcarbamoyl-6-succinylamino-3,7-dimethylamino-10H-phenothiazine | 668 |
| 10 | Bis[3-bis(4-chlorophenyl)methyl-4-disulfopropylaminophenyl]amine | 670 |
| 11 | Diaminobenzidine | 435 |
| 12 | o-Toluidine | 650 |
| 13 | 10-N-Methylcarbamoyl-3-dimethylamino-7-hydroxy-10H-phenoxazine | 520 |
| 14 | 3,3'-Dibromo-4,4'-dihydroxydiphenylamine | 590 |

The composition of the present invention may be in any preparation form so far as the compounds of the formulas (1) and (2) can react as the substrate for the peptidase enzyme from the specimen and the liberated enhancer can react to enhance the oxidation reaction of the chromogen with the oxidase.

Basically, the composition may be a combination of an aqueous solution containing the compound of the formula (1) or (2) or a mixture of the compounds of the formulas (1) and (2) and an aqueous solution containing both oxidase and chromogen, or the compound of the formula (1) or (2) or a mixture thereof and an aqueous solution containing both oxidase and chromogen. Preferably, the composition includes a buffer so that the determination can be carried out at pH of 5 to 9. There can be used any buffer which is usually used, for example, Good buffer, Tris-HCl buffer, phosphate buffer, borate buffer, acetate buffer, veronal buffer, HEPES buffer or the like. The aqueous solution can be prepared according to a conventional method, for example, by dissolving the compounds of the formulas (1) and (2), the chromogen, the oxidase and, if any, the buffer in distilled water. Further, optionally, other additives such as surfactants, preservatives, antibiotics and the like can be added.

In the reaction, preferably, the reagents can be used in the concentration of 0.01-10 mg/ml of the chromogen, 0.001-1,000 u/ml of the oxidase and 1 mM-1 M of the buffer, when 10 nM-10 mM of the compounds of the formulas (1) and (2) are used in the compounding ratio of 1:10-10:1.

The above-mentioned aqueous solutions can be prepared in the form that the solutions contain the compounds of the formulas (1) and (2), the chromogen, the oxidase and, if any, the buffer in the above desired concentrations, and can be directly used for a test. Alternatively, the solutions can be prepared in the form of concentrated solutions which can be optionally diluted with distilled water to give solutions in the desired concentrations before use.

The composition of the present invention includes solid preparations, for example, dried powder or granules obtained from the above-mentioned aqueous solution according to a known method, a powder mixture obtained by mixing powder ingredients, granules obtained from such a powder mixture, or liquid preparations soaked in carriers such as filter paper, paper disc, sheet, film, stick, sponge, polymers and the like. Further, it may be a kit.

When a test is carried out using the composition of the present invention, firstly, a specimen is collected. The specimen can be collected according to a known process. For example, gingival crevicular fluid and saliva can be collected with filter paper; capillary, paper point and the like, and dental plaque can be collected with a swab, curette, scaler and the like.

Then, the composition of the present invention is contacted with the specimen, for example, in a test tube, microtiter plate, cell, vial, plastic cuvette or the like to conduct the reaction, preferably, at pH of 5 to 9. This reaction is usually conducted at 20° to 45° C. The reaction time varies depending on a particular specimen and reaction temperature. Preferably, the reaction is carried out for 5 minutes to 24 hours.

After completion of the reaction, the presence of color development or its intensity is evaluated with the naked eye or with a spectrophotometer to determine the presence or intensity of peptidase enzymatic activity in the specimen. Thus, contraction or progress of periodontal diseases can be diagnosed or prognosticated, or therapeutic effect can be diagnosed.

The following Experiments and Examples further illustrate the present invention in detail.

Experiment 1

Peptidase enzymatic activity of the various kinds of oral anaerobes

Oral anaerobes, i.e., four strains of *Treponema denticola*, five strains of *B. gingivalis*, four strains of *Actinobacillus actinomycetemcomitans*, two strains of *Actinomyces israelii* and three strains of *Fusobacterium nucleatum* were tested for hydrolytic activity to the substrate of peptidase enzyme as follows.

The strains of Treponema were anaerobically cultivated using TYGVS media at 37° C. for 7 days, while other bacterial strains were cultivated using brain heart infusion broth at 37° C. for 48 to 72 hours. Each culture was diluted to obtain a bacterial cell suspension, the absorption at 660 nm of which was 0.5.

Substrate compounds for peptidase enzyme having DBHA as an enhancer were dissolved in 0.1 M Tris-HCl buffer (pH 7.5) at the concentration of 0.2 mM to obtain substrate solutions.

Separately, 0.1 M DIPSO buffer (pH 7.5) containing 5 mg/ml Dispanol M-32A was mixed with a compound P-2 and AOD to obtain the concentration of 0.2 mg/ml and 50 U/ml, and the resultant was used as a reagent A.

To the substrate solution (1.0 ml) were added the reagent A (1.5 ml) and the cell suspension (0.2 ml) and reacted at 37° C. for 30 minutes. After completion of the reaction, the absorption at 630 nM by the produced pigment was determined with a spectrophotometer.

On the basis of the average amount of $\Delta OD_{630}$, the peptidase enzymatic activity of each cell suspension was expressed as follows:

−: $\Delta OD_{630} < 0.05$
±: $0.05 < \Delta OD_{630} < 0.1$
+: $0.1 < \Delta OD_{630} < 0.5$
++: $0.5 < \Delta OD_{630} < 1.0$
+++: $1.0 < \Delta OD_{630} < 2.0$
++++: $2.0 \leq \Delta OD_{630}$ The results are shown in Table 1. Abbreviations used in Table 1 means the following substrate compounds.
GR: glycyl-arginine-DBHA
Bz-GR: N-benzoyl-glycyl-arginine-DBHA
Z-VGR: N-carbobenzoxy-valyl-glycyl-arginine-DBHA
GP: glycyl-proline-DBHA
Z-KP: N-carbobenzoxy-lysyl-proline-DBHA
Bz-RGFP: N-benzoyl-arginyl-glycyl-phenylalanyl-proline-DBHA suspensions, the absorption at 660 nm of which was 0.5 and 0.1.

As substrates, N-benzoyl-arginyl-glycyl-phenylalanyl-proline-DBHA (Bz-Arg-Gly-Phe-Pro-DBHA) and N-carbobenzoxy-glycyl-glycyl-arginine-DBHA (Z-Gly-Gly-Arg-DBHA) were used and dissolved in 0.1 M phosphate buffer (pH 7.0) at the concentration of 0.2 mM to prepare the substrate solution.

The determination of enzymatic activity according to the present invention was conducted according to the same manner as described in Experiment 1, wherein P-1 was used instead of P-2 as the chromogen.

Separately, as the conventional method, bacterial cell suspension (0.2 ml) was added to 0.2 mM substrate solution (1.0 ml). After completion of the reaction at 37° C. for 30 minutes, 12 mg/ml N-ethyl-N-(3-methylphenyl)-N'-succinyl ethylene diamine (EMSE) (1.0 ml) and 0.5 mg/ml potassium ferricyanide (0.5 ml) were added. After reaction at 37° C. for 5 minutes, the change of

TABLE 1

| Strain | Substrate | | | | |
|---|---|---|---|---|---|
| | GR | Bz—GR | Z—VGR | GP | Z—KP |
| Treponema denticola | + | ++ | +++ | ++ | + |
| Bacteroides gingivalis | ++ | +++ | +++ | +++ | ++ |
| Actinobacillus actinomycetemcomitans | − | − | − | − | − |
| Actinomyces israelii | − | − | − | − | − |
| Fusobacterium nucleatum | − | − | − | − | − |
| | Bz—RGFP | GR + GP | Bz—Gr + Z—KP | Z—VGR + Bz—RGFP | Bz—GR + Bz—RGFP |
| Treponema denticola | + | +++ | +++ | ++++ | +++ |
| Bacteroides gingivalis | ++ | +++ | ++++ | ++++ | ++++ |
| Actinobacillus actinomycetemcomitans | − | − | − | − | − |
| Actinomyces israelli | − | − | − | − | − |
| Fusobacterium nucleatum | − | − | − | − | − |

As is shown in Table 1, among the oral anaerobes, pathogenic spirochetes for periodontal diseases (*Treponema denticola*) and *B. gingivalis* show specific peptidase enzymatic activity. When the substrate having Arg at the C-terminal thereof is used together with the substrate having Pro at the C-terminal thereof, the enzymatic activity is increased twice or three times as much as that obtained by using either substrate alone.

Experiment 2

Comparison of sensitivity of the present method and that of a conventional method absorbance by produced pigment at 710 nm was determined by a spectrophotometer.

The results are shown in Table 2. The data were OD values determined by the conventional method and the method of the present invention.

As is obvious from the table, any combination of the two substrates and the cell solution, OD value obtained by the present method is 15 to 20 times as much as that obtained by the conventional method. Further, those undetectable by the conventional method due to a small amount of bacterial (enzyme) can be detected by the present method.

TABLE 2

| Strain | Amount of Bacteria $OD_{660}$ | Bz—Arg—Gly—Phe—Pro—DBHA | | Z—GLY—GLY—ARG—DBHA | |
|---|---|---|---|---|---|
| | | Conventional Method $OD_{710}$ | Present Method $OD_{630}$ | Conventional Method $OD_{710}$ | Present Method $OD_{630}$ |
| B. gingivalis | 0.1 | 0.01 | 0.02 | 0.08 | 2.25 |
| | 0.5 | 0.13 | 2.52 | 0.41 | 8.84 |
| Treponema denticola | 0.1 | 0 | 0.08 | 0.01 | 0.24 |
| | 0.5 | 0.03 | 0.44 | 0.06 | 1.32 |

Peptidase enzymatic activities of *Treponema denticola* ATCC35405 and *B. gingivalis* ATCC33277 were determined according to the method of the present invention and a conventional method, and sensitivities of the two methods were compared.

Cultivation of the bacteria was conducted according to the same manner as described in Experiment 1. The culture medium was diluted to prepare bacterial cell Experiment 3

According to the same manner as described in Experiment 2, sensitivities of the method of the present invention and the conventional method were compared except that the cell solution of *B. gingivalis* prepared in Experiment 2 so that its absorbance at 660 nm was 0.5 and the compound P-2 as the chromogen were used and various oxidases were used instead of AOD. Sensitivity was expressed as a ratio of $OD_{630}$ (the present method) to $OD_{710}$ (the conventional method).

The results are shown in Table 3. When various oxidases were used instead of AOD, higher sensitivity compared to the conventional method was obtained.

TABLE 3

| Oxidase | Concentration of Oxidase (U/ml) | Ratio of Sensitivity |
|---|---|---|
| MPO | 0.2 | 16.5 |
| CAO | 1.2 | 78.1 |
| Laccase | 0.05 | 4.3 |
| APO | 0.02 | 6.9 |
| HAO | 2.5 | 9.2 |
| PMO | 0.08 | 11.6 |
| BLOD | 0.02 | 5.2 |

Experiment 4

According to the same manner as described in Experiment 3, sensitivity of the method of the present invention was compared to that of the conventional method except that AOD was used as the oxidase, and, as the enhancer, SPA, DIHA, DSDA, PPD, DAS, MDBHA, DMDCHA, SDBA, EHDBA and DEDHA were used instead of DBHA.

As the result, the ratio of the sensitivity shown in Table 4 was obtained.

TABLE 4

| Enhancer | Ratio of Sensitivity |
|---|---|
| SPA | 5.2 |
| DIHA | 46.1 |
| DSDA | 3.4 |
| PPD | 6.8 |
| DAS | 4.4 |
| MDBHA | 16.6 |
| DMDCHA | 20.8 |
| SDBA | 5.0 |
| EHDBA | 11.4 |
| DEDHA | 8.9 |

Experiment 5

Correlation with clinical state (1)

Specimens of gingival crevicular fluid were collected with paper points from five subjects who were considered to be healthy based on their clinical state, six subjects with gingivalis and six subjects with periodontitis. Each specimen was dispersed in Ringer's solution (1.5 ml), and the relative amount of spirochete to total bacteria was determined with a phase contrast microscope according to the following equation:

$$\text{Relative amount} = \frac{\text{Number of spirochetes in 1 ml of Ringer's solution}}{\text{Number of all bacteria in 1 ml of Ringer's solution}} \times 100\,(\%)$$

Further, the Ringer's solution (0.2 ml) was tested for hydrolytic activity using the substrate solution prepared in the same manner as described in Experiment 1. As the substrate, there were used compounds of the formula (1), i.e., glycyl-proline-DBHA (GP) and N-benzoyl-arginyl-glycylphenylalanyl-proline-DBHA (Bz-RGFP) and compounds of the formula (2), i.e., N-carbobenzoxy-valyl-glycyl-arginine-DBHA (Z-VGR), N-benzoyl-glycyl-arginine-DBHA (Bz-GR) were used alone or in combination thereof.

The results are shown in Table 5. In Table 5, enzymatic activity was expressed in the same manner as in Experiment 1.

As shown in Table 5, enzymatic activity has correlation with the amount of spirochete and the clinical state. When the substrates are used in combination thereof, the activity is increased compared with that obtained by using the substrate alone.

TABLE 5

| | | Substrate | | | | | |
|---|---|---|---|---|---|---|---|
| Subject | Amount of Spirochete (%) | Z—VGR | Bz—GR | GP | Bz—RGFP | Z—VGR + GP | Bz—GR + B—RGFP |
| Healthy | | | | | | | |
| 1 | 0.3 | − | − | − | − | − | − |
| 2 | 1.4 | + | ± | ± | + | + | + |
| 3 | 0.5 | − | − | − | − | − | − |
| 4 | 0.2 | − | − | − | − | − | − |
| 5 | 1.2 | − | − | ± | − | ± | ± |
| Gingivitis | | | | | | | |
| 1 | 5.4 | + | + | + | + | + | + |
| 2 | 10.3 | + | + | + | + | ++ | ++ |
| 3 | 18.7 | ++ | + | ++ | ++ | ++ | ++ |
| 4 | 3.4 | − | − | − | − | − | − |
| 5 | 6.9 | − | ± | ± | − | ± | ± |
| 6 | 9.4 | + | ± | + | + | + | ++ |
| Periodontitis | | | | | | | |
| 1 | 20.5 | +++ | ++ | +++ | +++ | ++++ | ++++ |
| 2 | 35.4 | +++ | ++ | +++ | +++ | ++++ | ++++ |
| 3 | 29.3 | +++ | ++ | +++ | +++ | ++++ | ++++ |
| 4 | 25.3 | +++ | ++ | ++ | +++ | ++++ | ++++ |
| 5 | 40.5 | +++ | ++ | +++ | +++ | ++++ | ++++ |
| 6 | 39.7 | +++ | ++ | +++ | +++ | ++++ | ++++ |

Experiment 6

Correlation with clinical state (2)

A saliva mixture collected from a group of ten healthy subjects, a group of ten subjects with adult periodontitis or a group of four subjects with localized juvenile periodontitis was centrifuged to obtain a supernatant. The supernatant was used as a specimen and peptidase enzymatic activity obtained by the method of the present invention was compared with that obtained by the conventional method according to the same manner as described in Experiment 2. In this experiment, the reaction was conducted for 15 minutes. As the substrates, there were used N-carbobenzoxy-glycylarginine-DIHA (Z-GR), N-benzoylarginyl-glycyl-phenylalanyl-proline-DIHA (Bz-RGFP), alone or in combination thereof.

The results are shown in Table 6. Similar to Experiment 2, the results are expressed as $OD_{630}$ and $OD_{710}$.

As shown in Table 6, both groups of subjects with adult periodontitis and localized juvenile periodontitis have higher activity than that of health subjects in both methods, and difference is statistically significant. Further, in the method of the present invention, OD value is ten times as high as that of the conventional method and there is significant difference in OD values between the diseased groups and the health group. Particularly, using the substrate having arginine at the C-terminal together with the substrate having proline at the C-terminal, the diseased group showed more than about 1.5 times higher activity. Therefore, by determination of enzymatic activity according to the method of the present invention, periodontal diseases may be promptly diagnosed or prognosticated and therapeutic effect can be objectively evaluated.

TABLE 6

| | | Group | | |
|---|---|---|---|---|
| Method | Substrate | Healthy subjects | Adult Periodontitis subjects | Localized juvenile periodontitis subjects |
| Conventional Method ($OD_{710}$) | Z—GR | 0 ± 0 | 0.1 ± 0.1** | 0.1 ± 0.1** |
| | Bz—RGFP | 0 ± 0 | 0.1 ± 0.1** | 0.1 ± 0.1** |
| | Z—GR + B—RGFP | 0 ± 0 | 0.2 ± 0.1** | 0.1 ± 0.1** |
| Present Method ($OD_{630}$) | Z—GR | 0.1 ± 0.1 | 1.4 ± 0.6* | 1.0 ± 0.3** |
| | Bz—RGFP | 0.1 ± 0.1 | 1.2 ± 0.5* | 0.8 ± 0.3* |
| | Z—GR + B—RGFP | 0.2 ± 0.1 | 1.9 ± 0.6* | 1.5 ± 0.6* |

*$P < 0.01$
**$P < 0.05$

Example 1

As the substrate solution, a solution of N-carbobenzoxy-valyl-glycyl-arginine-DBHA in distilled water (2 mM) was prepared. 0.1 M Tris-HCl buffer (pH 7.0) was prepared and used as buffer A. 0.1 M DIPSO buffer (pH 7.5) containing Dispanol M-32A (5 mg/ml) was used as buffer B. AOD was added to buffer B to 200 U/ml and was used as the oxidase solution. The compound P-3 was dissolved in buffer B to 0.4 mg/ml and was used as the chromogen solution.

These reagents were combined and used as a kit for testing periodontal diseases.

This kit can be used for diagnosis or prognostication of periodontal diseases as follows.

A paper point is inserted into the gingival crevice of a subject for 30 seconds to collect a specimen. The substrate solution (0.1 ml) and the buffer A (0.9 ml) are mixed and the specimen is added to the mixture. The mixture is allowed to react at 37° C. for 30 minutes. To the resultant are further added the oxidase solution (0.5 ml) and the chromogen solution (0.5 ml), and the mixture is allowed to react at 37° C. for 30 minutes. After completion of the reaction, a color tone is observed by the naked eye. The intensity of blue color is evaluated by comparing with a blank control. Heavy blue color shows that the subject has periodontal diseases.

Example 2

The substrate reagent was prepared by soaking a paper disc (diameter:0.6 cm) with N-carbobenzoyl-glycylglycyl-arginine-SPA (500 nmol) and N-benzoyl-prolyl-alanylglycylproline-SPA (500 nmol). 0.1 M phosphate buffer (pH 7.0) containing Triton X-100 at 5 mg/ml was used as buffer C. A paper disc (diameter:0.6 cm) soaked with BLOD (0.02U) and the compound P-4 (1 mg) was used as the color producing reagent. These reagents were combined and used as a kit for testing periodontal diseases of the present invention.

This kit can be used for diagnosis or prognostication of periodontal diseases as follows.

The buffer solution C (400 μl) is placed in a vial to which are added saliva mixture (100 μl) collected from a subject and the paper disc of the substrate reagent. The mixture is allowed to react at 37° C. for 15 minutes. Further, a paper disc of the color producing reagent is added and allowed to react at 37° C. for 15 minutes. After completion of the reaction, the color development is evaluated by the naked eye according to the same manner as described in Example 1.

Example 3

N-Carbobenzoyl-arginine-DIHA (500 nmol), N-benzoylalanyl-proline-DIHA (250 nmol), HAO (2.5 U) and the compound P-5 were mixed and lyophilized in an ampoule (inner diameter:5 mm; length:3 cm) to prepare the reaction reagent.

0.1 M DIPSO buffer (pH 7.5) containing Triton X-100 (5 mg/ml) was prepared and used as a buffer.

These reagents were combined and used as the kit for testing periodontal diseases of the present invention.

This kit can be used for diagnosis or prognostication of periodontal diseases as follows.

A paper strip is inserted into the gingival crevice of a subject for 30 seconds to collect a specimen. The buffer (1 ml) is poured in an ampoule containing reagent to dissolve it. The specimen is added to the solution and reacted at 37° C. for 30 minutes. After completion of the reaction, the color development is evaluated with the naked eye according to the same manner as described in Example 1.

Example 4

N-t-Butoxycarbonyl-valyl-leucyl-glycyl-arginine-DBHA, MPO, the compound P-8 (5 mg/ml) were dissolved in 0.1 M-DIPSO buffer (pH 7.5) containing dispanol M32A in the concentration of 20 nmol/ml, 0.2 U/ml, 0.2 mg/ml, respectively. A circular filter paper (diameter:1 cm) was soaked with the solution (100 μl), dried to prepare a test paper.

This test paper can be used for diagnosis or prognostication of periodontal diseases as follows.

Saliva mixture (100 μl) collected from a subject is added dropwise to the test paper and reacted at room temperature for 20 minutes. After completion of the reaction, the color tone of the test paper is evaluated with the naked eye. Comparing to the control sample which is prepared by adding water instead of the specimen, the intensity of blue color is evaluated. Strong blue shows that the subject have periodontal diseases.

Example 5

AOD (3000 U) was lyophilized in a vial (shell diameter:30 mm; length:60 m) and used as reagent A1 (for 30 specimens).

N-Carbobenzoxy-glycyl-glycyl-arginine-DBHA (50 nmol) and the compound P-7 (0.5 mg) were mixed and lyophilized in a vial (shell diameter:18 mm; length:33 mm) and used as reagent A2 (for one specimen).

0.1 MPIPES buffer (pH 7.0) containing 1 ml/ml dispanol (30 ml) was charged in a pet bottle (75 ml volume) and used as reagent B (for 30 specimens).

An aqueous solution containing sodium diethyldithiocarbamate (5 mg/ml) and sodium nitride (2 mg/ml) (pH 9.5) was charged in an eye drop bottle (50 ml volume) and used as a reaction terminator solution.

These reagents were combined and used as kit for testing periodontal diseases of the present invention.

This kit can be used for diagnosis or prognostication of periodontal diseases as follows.

A bottle of reagent A1 is dissolved with a bottle of reagent B1 to prepare AOD solution. A paper point is inserted into the gingival crevice of a subject for 30 seconds to collect a specimen and poured in a vial containing reagent A2. To the mixture is added AOD solution (1 ml). After 15 minutes, the reaction terminator solution (one drop) is added and the mixture is stirred to stop the reaction. After addition of the reaction terminator solution, color development is observed with the naked eye within 4 hours in the same manner as described in Example 1.

What is claimed is:

1. A composition for testing periodontal diseases by determining peptidase enzymatic activity in a specimen, comprising:

(a) a compound of the formula:

X-T-B-Y wherein B is a residue of proline or arginine;
X is hydrogen or an amino protecting group;
Y is attached to the C-terminal of B and is a residue of an aniline derivative of the formula:

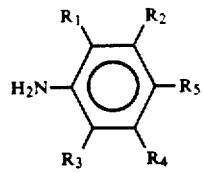

wherein
$R_1$-$R_4$ are the same or different and are hydrogen, halogen, alkyl having 1 to 4 carbon atoms, sulfone or hydroxyl; and $R_5$ is hydroxyl, amino or amino substituted with alkyl having 1 to 4 carbon atoms, sulfoalkyl having 1 to 4 carbon atoms or hydroxylalkyl having 1 to 4 carbon atoms, or diaminostilbendisulfonic acid; and
T is a single bond, an amino acid or peptide residue composed of up to 4 amino acids, the C-terminal of which is attached to the N-terminal of B;

(b) a chromogen which develops color by oxidation selected from the group consisting of 10-N-Methylcarbamoyl-3,7-dimethylamino-10H-phenothiazine, 10-N-Carboxymethylcarbamoyl-6-nitro-3,7-dimethylamino-10H-phenothiazine and 10-N-Carboxymethylcarbamoyl-6-succinylamino-3,7-dimethylamino-10H-phenothiazine; and (c) an oxidase, the aniline derivative being an enhancer which is capable of increasing the oxidation reaction rate of the chromogen with the oxidase, compound (a) and the oxidase being present in amounts sufficient to result in oxidation of the chromogen in the presence of peptidase in the specimen, the chromogen being present in an amount sufficient to produce a detectable color change when oxidized.

2. A composition for testing for periodontal diseases according to claim 1, wherein B is proline and the C-terminal amino acid residue in the group T is a residue of glycine, alanine, lysine or phenylalanine.

3. A composition for testing for periodontal diseases according to claim 1, wherein B is arginine and the C-terminal amino acid residue in the group T is a residue of glycine, lysine, arginine or phenylalanine.

* * * * *